(12) United States Patent
Goldman

(10) Patent No.: US 8,420,398 B2
(45) Date of Patent: Apr. 16, 2013

(54) ESTROUS CYCLE MONITORING BY COLOR RESPONSE

(75) Inventor: Dorothee Goldman, Hammondsport, NY (US)

(73) Assignee: Oratel Diagnostics, LLC, Hammondsport, NY (US)

( * ) Notice: Subject to any disclaimer, the term of this patent is extended or adjusted under 35 U.S.C. 154(b) by 0 days.

(21) Appl. No.: 13/212,864

(22) Filed: Aug. 18, 2011

(65) Prior Publication Data

US 2012/0047587 A1    Feb. 23, 2012

Related U.S. Application Data

(63) Continuation of application No. PCT/US2011/046586, filed on Aug. 4, 2011.

(60) Provisional application No. 61/375,496, filed on Aug. 20, 2010, provisional application No. 61/421,853, filed on Dec. 10, 2010.

(51) Int. Cl.
*G01N 33/48* (2006.01)
*G01N 21/77* (2006.01)
*A61D 19/02* (2006.01)

(52) U.S. Cl.
USPC ............. 436/65; 436/63; 436/93; 436/164; 436/169; 422/400; 422/420; 600/35; 600/551

(58) Field of Classification Search .......... 436/63, 436/65, 86, 87, 93, 164, 166, 169; 422/400, 422/420, 430, 68.1, 82.05; 600/551, 35; 800/8
See application file for complete search history.

(56) References Cited

U.S. PATENT DOCUMENTS

| | | | |
|---|---|---|---|
| 4,358,288 A * | 11/1982 | Goldman | .......... 436/65 |
| 5,334,502 A | 8/1994 | Sangha | |
| 5,356,817 A | 10/1994 | Cole | |
| 5,922,613 A | 7/1999 | Goldman | |
| 5,981,291 A | 11/1999 | Goldman | |
| 6,294,349 B1 | 9/2001 | Streckfus | |
| 6,531,277 B2 | 3/2003 | Timms | |
| 6,645,725 B2 | 11/2003 | Yeaman | |
| 6,780,594 B2 | 8/2004 | Hess-Stump et al. | |
| 6,867,051 B1 | 3/2005 | Anderson et al. | |
| 6,972,180 B1 | 12/2005 | Streckfus et al. | |
| 2003/0166014 A1 | 9/2003 | Timms | |
| 2005/0220912 A1 | 10/2005 | Theoharides | |
| 2005/0240085 A1 | 10/2005 | Knoell et al. | |
| 2006/0013905 A1 | 1/2006 | Tehoharides | |
| 2008/0200379 A1 | 8/2008 | Tabibzadeh et al. | |
| 2008/0241852 A1 | 10/2008 | Messer et al. | |
| 2010/0267003 A1 | 10/2010 | Goldman | |
| 2010/0272637 A1 | 10/2010 | Schilling | |
| 2011/0015087 A1 | 1/2011 | Nagore Casas et al. | |

FOREIGN PATENT DOCUMENTS

| | | |
|---|---|---|
| WO | 96/29606 A1 | 9/1996 |
| WO | 00/47739 A2 | 8/2000 |
| WO | 2007/126982 A1 | 11/2007 |

OTHER PUBLICATIONS

S. Simoens, et al, "Endometriosis: cost estimates and methodological perspective", Hum Reprod Update 2007, pp. 395-404, Jul.-Aug. 13(4).
T, Price, et al, "Immunofluorescent Localization of a Novel Progesterone Receptor(s) in a T47D-Y Breast Cancer Cell Line Lacking Genomic Progesterone Receptor Expression", J Soc Gynecol Investig, Dec. 2005, pp. 610-616, vol. 12, No. 8.
B. Kay, et al, "The importance of being proline: the interaction of proline-rich motifs in signaling proteins with their cognate domains", The FASEB Journal. Feb. 2000, pp, 231-241, vol. 14.
V. Boonyaratanakornkit, et al, "Progesterone Receptor Contains a Proline-Rich Motif that Directly Interacts with SH3 Domains and Activates c-Src Family Tyrosine Kinases", Molecular Cell, Aug. 1, 2001, pp. 269-280, vol. 8.
G. Proctor, et al, "The Function of Salivary Proteins and the Regulation of Their Secretion by Salivary Glands", Biomed Rev, 1998, pp. 3-15, vol. 9.
P.G. Groothuis, et al, "Estrogen and the endometrium: lessons learned from gene expression profiling in rodents and human", Human Reproduction Update, 2007, pp. 405-417, vol. 13. No. 4.
K. Pettersson, et al, "Role of Estrogen Receptor Beta in Estrogen Action", Annual Review of Physiology, 2001, pp. 165-192, vol. 63.
P. Calias, et al, "Synthesis of inositol 2-phosphate-quercetin conjugates". Carbohydrate Research, 1996 pp. 83-90, vol. 292.
E. Markou, et al, "The Influence of Sex Steroid Hormones on Gingiva of Women", The Open Dentistry Journal, 2009, pp. 114-119, vol. 3.
G. Attia, et al, "Progesterone Receptor Isoform A But Not B Is Expressed in Endometriosis", The Journal of Clinical Endocrinology & Metabolism, 2000, pp. 2897-2902, vol. 85, No. 8.
J. Aplin, "MUC-1 glycosylation in endometrium: possible roles of the apical glycocalyx at implantation", Human Reproduction, 1999, pp. 17-25, vol. 14 (Suppl. 2).
S. Hild-Petito. "Mucin (Muc-1) Expression is Differentially Regulated in Uterine Luminal and Glandular Epithelia of the Baboon (Papio anubis)"; Biology of Reproduction, 1996, pp. 939-947, vol. 54.
P. Sarni-Manchado, et al, "Infuence of the Glycosylation of Human Salivary Proline-Rich Proeins on Their Interactions with Condensed Tannins" J. Agric. Food Chem., 2008, pp. 9563-9569, vol. 56.

(Continued)

*Primary Examiner* — Maureen Wallenhorst
(74) *Attorney, Agent, or Firm* — Berenato & White, LLC

(57) ABSTRACT

A method of determining the phase of an estrous cycle that a mammal is in at a given time that a biological sample is obtained from the mammal is provided. The biological sample obtained from the mammal is combined with at least one flavonoid pigment that reacts with the biological sample on a hydrophobic surface to provide a color response. The estrus phase of the estrous cycle has a corresponding color response that is distinguishable from the color response of each other phase of the estrous cycle to an unaided human eye. The corresponding color response is correlated to the estrus phase of the estrous cycle.

Figure 1:
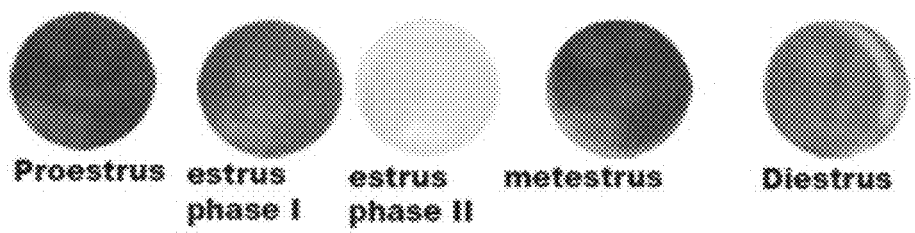

18 Claims, 3 Drawing Sheets
(3 of 3 Drawing Sheet(s) Filed in Color)

OTHER PUBLICATIONS

A. Rodgers, et al, "Inhibition of CD44 N- and O-linked Glycosylation Decreases Endometrial Cell Lines Attachment to Peritoneal Mesothelial Cells", Fertil Steril., Feb. 2011, pp. 823-825. vol. 95, No. 2.

A. Van Nieuw Amerongen, et al, "Salivary Proteins: Protective and Diagnostic Value in Cariology?", Caries Research, 2004, pp. 247-253, vol. 38.

G.B. Proctor, et al, "Salivary Proteins Interact with Dietary Constituents to Modulate Tooth Staining", Journal of Dental Research, 2005, vol. 84, No. 1, 1 page Abstract.

H. Zhang, et al, "Use of proteomic analysis of endometriosis to identify different protein expression in patients with endometriosis versus normal controls", Fertility and Sterility, Aug. 2006, pp. 274-282, vol. 86, No. 2.

L. Margarit, et al, "MUC1 as a Discriminator between Endometrium from Fertile and Infertile Patients with PCOS and Endometriosis", J Clin Endocrinol Metab, Dec. 2010, pp. 5320-5329, vol. 95, No. 12.

A. Bennick, et al, "The Nature of the Hydroxyapatite-Binding Site in Salivary Acidic Proline-Rich Proteins", Biochem. J., 1979, pp. 115-126, vol. 183.

G. Madapallimattam, et al, "Phosphopeptides derived from human salivary acidic proline-rich proteins", Biochem. J., 1990, pp. 297-304, vol. 270.

B. Sengupta, et al, "The interaction of quercetin wth human serum albumin: a fuorescence spectroscopic study", Biochemical and Biophysical Research Communications, 2002, pp. 400-403, vol. 299.

C. Dufour, et al, "Flavonoid-serum albumin complexation: determination of binding constants and bindling sites by fluorescence spectroscopy", Biochemical and biophysical research communications. 2002, vol. 299, No. 3, 1 page Abstract.

B. Delvoux, et al, "Increased Production of 17 beta-estradiol in Endometriosis Lesions is the Result of Impaired Metabolism", J Clin Endocrinol Metab., Mar. 2009, pp. 878-883, vol. 94, No. 3.

M. Meseguer, et al, "MUC1 and endometrial receptivity". Molecular Human Reproduction, 1998, pp. 1089-1098, vol. 4, No. 12.

Byoung-Moo Seo, et al, "Investigation of multipotent postnatal stem cells from human periodontal ligament", The Lancet, Jul. 10, 2004, vol. 364, issue 9429, 2 pp Summary.

H. Taylor, "Endometrial cells derived from donor stern cells in bone marrow transplant recipients", JAMA, 2004, vol. 292, No. 1, 2 pp Abstract.

K. Sakabe, et al, "Progestin and estrogen receptors: characterization and localization in rat submandibular glands, with special reference to epidermal growth factor", Endocrinol Jpn., Oct. 1988, vol. 35, No. 5, 1 pg. Abstract.

A. Zalewska, et al, "Structure and biosynthesis of human salivary mucins", Acta Biochimica Polonica, 2000, vol. 47, No. 4, pp. 1067-1079.

Gargett, "Uterine stem cells: What is the evidence?", Human Reproduction Update, 2007, pp. 87-101, vol. 13, No. 1.

J, Ai, et al, "Endometrial Stem Cells and Endometriosis", http://www.intechopen.com/books/endometriosis-basic-concepts-and-current-research-trends/endometrial-stem-cells-and-endometriosis, pp. 297-308.

Lori, et al,"Mechanism for the Adsorption of Mucin on Hydroxyapatite" Nigerian Journal of Chemical Research, 2005, pp. 21-29. vol. 10.

A. Fukushima, et al, "Role of Na+ and Ca2+ Channels in the Preoptic LH Surge Generating Mechanism in Proestrous Rats", Endocrine Journal, 2003. pp. 145-153, vol. 50, No. 2.

G. Proctor, et al, "The Function of Salivary Proteins and the Regulation of Their Secretion by Salivary Glands", Biomedical Reviews, 1998, pp. 3-15, vol. 9.

V. Braga, et al, "Modulation of Muc-1 mucin expression in the mouse uterus during the estrus cycle, early pregnancy and placentation", Journal of Cell Science, 1993, pp. 397-405, vol. 105.

B, Madhan, et al, "A Semi-Empirical Quantum Mechanical Modeling Study on the Interaction of Collagen-like Peptides with Polyphenolic Molecules: An Attempt to Gain Insights into Vegetable Tanning", JALCA, 2003, pp. 272-277, vol. 98.

S. Chiappin, et al., "Saliva specimen: A new laboratory tool for diagnostic and basic investigation", Clinica Chimica Acta 383. 2007, pp. 30-40.

International Search Report and Written Opinion mailed Mar. 8, 2012, International Application No. PCT/US11/46586.

International Search Report, International Application No. PCT/US2012/046175, mailed Oct. 5, 2012, 4pp.

E. Attar et al, "Aromatase and other steroidogenic genes in endometriosis: translational aspects", Human Reproduction Update, 2006, pp. 49-56, vol. 12 No. 1.

T. Ediger et al, "Estrogen Receptor Regulation of the Na+/H+ Exchanger Regulatory Factor", Endocrinology, 2009, pp. 2976-2982, vol. 140 No. 7.

L. Sevon et al, "Effect of Age on Flow-Rate, Protein and Electrolyte Composition of Stimulated Whole Saliva in Healthy, Non-Smoking Women", The Open Dentistry Journal, 2008, pp. 89-92.

L.C. Kao et al, "Expression Profiling of Endometrium from Women with Endometriosis Reveals Candidate Genes for Disease-Based Implantation Failure and Infertility", Endocrinology, 2003, pp. 2870-2881, vol. 144 No. 7.

S. Parkkila et al, "Immunohistochemical Localization of Carbonic Anhydrase Isoenzymes VI, II and I in Human Parotid and Submandibular Glands", The Journal of Histochemistry and Cytochemistry, 1990, pp. 941-947, vol. 38 No. 7.

E. Szmuilowicz et al, "Relationship between Aldosterone and Progesterone in the Human Menstrual Cycle", The Journal of Endocrinology & Metabolism, 2006, pp. 3981-3987, vol. 91 No. 10.

C.A.B. Clemetson et al, "The Effects of Oestrogen and Progesterone on the Sodium and Potassium Concentrations of Rat Uterine Fluid", Journal of Endocrinology, 1970, pp. 309-319, vol. 47, 1 page Abstract.

S. Bulun et al, "Endometriosis", New England Journal of Medicine, Jan. 15, 2009, pp. 268-279, vol. 360 No. 3.

Research Projects, "Theory and modelling", 6 pages.

C. Hannig et al, "Transaminases in the acquired pellicle", Archives of Oral Biology, May 2009, pp. 445-448, vol. 54 No. 5, 2 pages Abstract.

G. Fia et al, "Prediction of grape polyphenol astringency by means of a fluorimetric micro-plate assay", Food Chemistry, Mar. 2009, pp. 325-330, vol. 113 No. 1, 2 pages Abstract.

R.M. Nagler et al, "Salivary glands and the aging process: mechanistic aspects, health-status and medicinal-efficacy monitoring", Biogerontology, 2004, pp. 223-233, vol. 5, 1 page Abstract.

N. Stachenfeld et al, "Progesterone increases plasma volume independent of estradiol", Journal of Applied Physiology, 2005, pp. 1991-1997, vol. 98.

"Saliva may paint an insightful view of the body's health", Jun. 12, 2005, http://www.medilexicon.com/medicalnews.php?newsid=26004.

D. Goldman, "A discussion about pH patterns and absorbency patterns for malividin 3,5 digluocside mixed with saliva samples from a woman with endometriosis and a woman who does not have endometriosis and a comparison of estradiol levels in saliva to pH patterns and to optical density patterns", Mar. 20, 2006, 14 pages.

Bedaiwy et al, "Prediction of endometriosis with serum and peritoneal fluid markers: a prospective controlled trial", Human Reproduction, 2002, pp. 426-431, vol. 17 No. 2.

Koshiba et al, "Expression of Allograft Inflammatory Factor-1 in Human Eutopic Endometrium and Endometriosis: Possible Association with Progression of Endometriosis", The Journal of Clinical Endocrinology & Metabolism, 2005, pp. 529-537, vol. 90 No. 1.

H. Valimaa et al, "Estrogen receptor-beta is the predominant estrogen receptor subtype in human oral epithelium and salivary glands", Journal of Endocrinology, 2004, pp. 55-62, vol. 180.

Ja-Mun Chong et al, "Interleukin 1beta Expression in Human Gastric Carcinoma with Epstein-Barr Virus Infections", Journal of Virology, Jul. 2002, pp. 6825-6831, vol. 76 No. 13.

C. Ballare et al, "Two Domains of the Progesterone Receptor Interact with the Estrogen Receptor and Are Required for Progesterone Activation of the c-Src/Erk Pathway in Mammalian Cells", Molecular and Cellular Biology, Mar. 2003, pp. 1994-2008, vol. 23 No. 6.

M.E. Baker, "Beyond Carrier Proteins Albumin, steroid hormones and the origin of vertebrates", Journal of Endocrinology, 2002, pp. 121-127, vol. 175.

S. Kavoussi et al, "Periodontal disesase and endometriosis: Analysis of the National Health and Nutrition Examination Survey", Fertility and Sterilility, Feb. 2009, pp. 335-342; vol. 91 No. 2.

J. Hu et al, "Carbonic Anhydrase Regulate Endometrial Gland Development in the Neonatal Uterus", Biology of Reproduction; 2005, pp. 131-138, vol. 73.

D. He et al, "Characterization of Proline-Serine-Rich Carboxyl Terminus in Human Sulfotransferase 2B1b: Immunogenicity, Subcellular Localization, Kinetic Properties, and Phosphorylation", Drug Metabolism and Disposition, pp. 1749-1755, vol. 34 No. 10, 2006.

M. C. Rose et al, "Respiratory Tract Mucin Genes and Mucin Glycoproteins in Health and Disease", Physiological Reviews, 2006, pp. 245-278, vol. 86.

G. Goobes et al, "Folding of the C-terminal bacterial binding domain in statherin upon adsorption onto hydroxyapatite crystals", PNAS, Oct. 31, 2006, pp. 16083-16088, vol. 103, No. 44.

N. Heldring et al, "Estrogen Receptors: How Do They Signal and What Are Their Targets", Physiological Reviews, 2007, pp. 905-931, vol. 87.

E. Azen et al, "Genetic Polymorphism of Proline-Rich Human Salivary Proteins", Science, Jun. 8, 1973, pp. 1067-1069; vol. 180, No. 4090, 1 page Abstract.

S. Senapati et al, "Mucin-interacting proteins: from function to therapeutics", Trends in Biochemical Sciences, Apr. 2010, pp. 236-245, vol. 35 No. 4.

International Search Report, International Application No. PCT/US2007/007803, mailed Jun. 9, 2007, 4pp.

* cited by examiner

| Cycle Phase | pigment color Mvg CaCl₂ | progesterone ng/ml plasma | estrogen ng/ml plasma | LH ng/ml plasma |
|---|---|---|---|---|
| | piece color appears | | | |
| | day-3 purple | | | |
| | day-2 pale purple | <4 ng/ml | >4×10-3 ng/mg | >2ng/ml |
| PROESTRUS 1-3 days | day-1 no color | | | |
| | | | increase to 10×10⁻³ng/ml | 4ng/ml |
| ESTRUS 6-36 hrs | 1st half aqua | <2 ng/ml | <2×10⁻³ng/ml | >10ng/ml |
| | 2nd half pale | | less than 2×10-4 ng/ml | <2ng/ml |
| METESTRUS 3-4 day | turbo pink | | increase to 6 ng/ml | <2ng/ml |
| | | increase to 4 ng/ml | | |
| DIESTRUS 13-15 days | blue purple | | near 2×10⁻³ ng/ml | |

Fig. 2

ESTROUS CYCLE MONITORING BY COLOR RESPONSE

CROSS REFERENCE TO RELATED APPLICATION(S)

This application is a continuation of PCT/US2011/046586 filed Aug. 4, 2011, and claims the benefit of priority of provisional application Nos. 61/375,496 filed Aug. 20, 2010 and 61/421,853 filed Dec. 10, 2010.

FIELD OF THE INVENTION

This invention relates to the monitoring of an estrous cycle, especially for the detection of the estrus phase of the cycle, preferably using non-invasive test procedures. The invention finds applicability in veterinary, breeding, experimental and other practices.

BACKGROUND

The successful monitoring of an estrous (also known as oestrous) cycle has many potential uses. For example, artificial insemination of animals, especially cattle and other livestock, as well as other mammals is often employed by dairy farmers and other animal caretakers for breeding. Successful impregnation requires that the artificial insemination procedure take place at the appropriate period within the animal's estrous cycle. Additionally, successful monitoring can allow breeding to be timed to coincide with the appropriate period of an animal's estrous cycle. Such timing may be especially important when, for example, a mare is to be transported to a stallion for breeding. Another example of a potential use for monitoring an estrous cycle is in connection with laboratory testing and studies. Accuracy of certain tests may depend on the administration of a drug or the performance of another procedure during a particular phase of the estrous cycle, or synchronization of testing on test animals so that the administration procedure is performed at the same phase of the subjects' estrous cycles.

The estrous cycle of a female mammal that reabsorbs the endometrium, in contrast to menstruation which releases the endometrium, as occurs in primates, involves recurring hormone-induced physiological changes and generally is characterized by four phases: proestrus, estrus, metestrus, and diestrus. During proestrus, prostaglandin $PF2\alpha$ causes regression of the corpus luteum developed in the previous cycle. As the corpus luteum is destroyed, there is a fall in progesterone levels. The fall in progesterone levels is accompanied by an increase in the production of follicle stimulating hormone (FSH), which stimulates follicular growth in the follicle that will result in ovulation. During this phase there is an increase in circulating estradiol levels.

The estrus phase refers to a periodic state of the estrous cycle in mammals that do not experience menstruation. The estrus phase has two stages. The first stage of the estrus phase is initiated as estradiol levels rise and cause the production of luteinizing hormone (LH). During this first stage of the estrus phase, which is also known as behavioral estrus or "heat," the estradiol levels will begin to decrease as the LH level surges to a maximum concentration or LH peak. The length of the behavioral expression of estrus (or "heat") varies from animal to animal. An example of a female mammal with spontaneous ovulation is the cow. Generally, subject to variations between individual animals, behavioral estrus in a cow lasts between 8-28 hours. The subsequent second stage of the estrus phase runs from the LH peak to ovulation. In cows, ovulation may occur approximately 12-18 hours after behavioral estrus or "heat" has ended. During this second stage of the estrus phase, successful inducement of pregnancy is most likely to occur.

Metestrus is a period of sexual inactivity following the estrus phase. Metestrus can last from 1-5 days as observed in the case of cows. In metestrus, early corpus luteum development begins anew in a process known as luteinization and progesterone levels begin to rise. Estradiol levels increase in cyclic phases during metestrus. Metestrus lasts until the beginning of the diestrus phase. During diestrus, estradiol varies in cyclic waves of about 4 days duration and levels of estradiol remain relatively low until proestrus, when the corpus luteum is destroyed through the action of prostaglandins such at $PF2\alpha$ which causes progesterone to fall and estradiol levels to increase to their maximal levels. The cycle thereby repeats itself.

Estrous cycle frequency and duration varies from species to species. Some species of mammals have spontaneous ovulation that comes in regular cycles. The estrous cycles of some species with spontaneous ovulation can also be seasonal. Some species have only one "heat" per season, while others may have multiple heats. Other types of mammal species have induced ovulation which is stimulated by the presence or contact with a male of the same species. Examples include rabbits, camels, and alpacas.

Failure to timely inseminate during the appropriate phase of the estrous cycle, preferably immediately before ovulation, creates a significant economic burden to the farmer. For seasonal breeders, for example, unsuccessful breeding can cause the breeder to wait weeks or months for another breeding opportunity. Further, the insemination and breeding procedures are themselves expensive, and repeating the procedures multiple times on the same animal for a single successful pregnancy can significantly increase costs. Furthermore, the delay inherent in waiting for the next estrus phase or seasonal estrous cycle to re-inseminate the animal compounds the economic burden on the breeder, especially if the animal produces milk, for which maximal production may be dependent on successful breeding and a continuous stream of pregnancies.

About half of all cow estrus phases fail to be observed because the farmer is either not present to actually observe the animal in estrus or because existing estrus detection tests are not sufficiently reliable. P. L. Senger, Estrus Detection Problem New Concepts Technologies and Possibilities, J. Dairy Science, 77:2745-2753 (1994). It has been estimated that failed insemination and breeding costs U.S. dairy farmers over $300 million annually. R. L. Wallace, Economic Efficiencies of Dairy Herd Reproductive Programs, DVM, MS Illinois Dairy Net Papers (Mar. 13, 2002). Hence, accurate and reliable detection of the estrus phase is highly important for high impregnation and breeding success rates and, ultimately, is highly important to farmers and other breeders for economic reasons.

Anthocyanin pigments can be used to measure fertility and estrogen-dependent physiological changes in females. U.S. Pat. Nos. 4,358,288, 5,922,613, and 5,981,291 describe the color response that an anthocyanin pigment produces when contacted with a body fluid such as saliva or vaginal fluid. It has now been observed by the present inventor that certain forms of anthocyanin pigments specified in the aforementioned patents, specifically 3,5-diglycosidyl anthocyanins, show near identical color responses to the unaided eye for both the fertile estrus phase and the mid-luteal phase (i.e., diestrus) of the estrous cycle when tested on a cellulose surface with no other agents. Because the likelihood of successful pregnancy when insemination or breeding in the mid-luteal phase is significantly lower than in the fertile estrus phase, it is desirable for an estrus phase detection test to be capable of distinguishing between these phases.

Commercial kits are available for estrus evaluation of female livestock and other mammals. These known commercial kits at best identify only the general phase of estrus; they do not distinguish between the first stage of the estrus phase (before the LH peak) and second stage of the estrus phase (after the LH peak). The second stage of the estrus phase is the optimal time period for insemination and breeding. Timing insemination or breeding to coincide with the second stage of the estrus phase is important for optimum pregnancy results. Insemination and breeding in the first stage of the estrus phase does not generate a pregnancy at nearly the rate of breeding as in the second stage of the estrus phase. Lack of clarity and consistency in known commercial kits results in inaccurate timing for insemination and breeding, causing lower pregnancy rates, increased costs, and decreased efficiency to the breeder.

Accordingly, it is highly desirable to have an estrus detection procedure that allows the inseminator/breeder to determine the estrus phase, and more desirably distinguish the optimal fertile stage of the estrus phase from other phases of the estrous cycle, including the mid-luteal and diestrus phases and desirably the first stage of the estrus phase, in order to efficiently and effectively determine whether the female is (or when the female will be) ready for insemination/breeding.

SUMMARY OF THE INVENTION

According to a first aspect of the invention, a method is provided of determining the phase of an estrous cycle that a mammal is in at a given time that a biological sample is obtained from the mammal. The biological sample obtained from the mammal is combined with an anthocyanin pigment and flavonol pigment to induce a reaction that provides a color response on a hydrophobic substrate. The estrus phase of the estrous cycle has a corresponding color response to the anthocyanin pigment and the flavonol that is distinguishable to an unaided human eye from the color responses of each other phase of the estrous cycle. The corresponding color response is correlated to the estrus phase of the estrous cycle. In an exemplary embodiment of this first aspect, the anthocyanin pigment has a three-position carbon with a first O-glycosyl group and a five-position carbon with a second O-glycosyl group. In another exemplary embodiment of the first aspect, the color response correlating to a first stage of the estrus phase of the estrous cycle prior to the LH peak is distinguishable to an unaided human eye from the color response correlating to a second stage of the estrus phase of the estrous cycle subsequent to the LH peak.

A second aspect of the invention provides a method of determining the phase of an estrous cycle that a mammal is in at a given time that a biological sample is obtained from the mammal. The biological sample obtained from the mammal is combined with an anthocyanin pigment and divalent metal salt solution to induce a reaction that provides a color response on a hydrophobic substrate. The estrus phase of the estrous cycle has a corresponding color response to the anthocyanin pigment and the divalent metal salt solution that is distinguishable to an unaided human eye from the color responses of each other phase of the estrous cycle. The corresponding color response is correlated to the estrus phase of the estrous cycle. In an exemplary embodiment of this second aspect, the anthocyanin pigment has a three-position carbon with an O-glycosyl group and a five-position carbon without an O-glycosyl group. In another exemplary embodiment of the second aspect, the color response correlating to a first stage of the estrus phase of the estrous cycle prior to the LH peak is distinguishable to an unaided human eye from the color response correlating to a second stage of the estrus phase of the estrous cycle subsequent to the LH peak.

A third aspect of the invention provides a method of determining the phase of an estrous cycle that a mammal is in at a given time that a biological sample is obtained from the mammal. The biological sample obtained from the mammal is combined with a flavonol and iodine to induce a reaction that provides a color response on a hydrophobic substrate. The estrus phase of the estrous cycle has a corresponding color response to the flavonol and the iodine that is distinguishable to an unaided human eye from the color responses of each other phase of the estrous cycle. The corresponding color response is correlated to the estrus phase of the estrous cycle. In an exemplary embodiment of this third aspect, the flavonol is quercetin.

A fourth aspect of the invention provides a method of inducing pregnancy in a mammal which exhibits an estrous cycle. The phase of an estrous cycle that the mammal is in at a given time that a biological sample is obtained from the mammal is monitored by combining the biological sample obtained from the mammal with an anthocyanin pigment and a flavonol pigment to induce a reaction that provides a color response on a hydrophobic substrate. The estrus phase of the estrous cycle has a corresponding color response to the anthocyanin pigment and the flavonol that is distinguishable to an unaided human eye from the color responses of each other phase of the estrous cycle. The mammal is inseminated or bred at a point in time when the mammal is indicated to be in the estrus phase as reflected by the color response. In an exemplary embodiment of this fourth aspect, the anthocyanin pigment has a three-position carbon with a first O-glycosyl group and a five-position carbon with a second O-glycosyl group. In another exemplary embodiment of the fourth aspect, the color response correlating to a first stage of the estrus phase of the estrous cycle prior to the LH peak is distinguishable to an unaided human eye from the color response correlating to a second stage of the estrus phase of the estrous cycle subsequent to the LH peak.

A fifth aspect of the invention provides a method of inducing pregnancy in a mammal which exhibits an estrous cycle. The method involves monitoring the phase of an estrous cycle that the mammal is in at a given time that a biological sample is obtained from the mammal. The monitoring involves combining the biological sample obtained from the mammal with an anthocyanin pigment and divalent metal salt solution to induce a reaction that provides a color response on a hydrophobic substrate. The estrus phase of the estrous cycle has a corresponding color response to the anthocyanin pigment and the divalent metal salt solution that is distinguishable to an unaided human eye from the color responses of each other phase of the estrous cycle. The mammal is inseminated or bred at a point in time when the mammal is indicated to be in the estrus phase as reflected by the color response. In an exemplary embodiment of this fifth aspect, the anthocyanin pigment has a three-position carbon with an O-glycosyl group and a five-position carbon without an O-glycosyl group. In another exemplary embodiment of the fifth aspect, the color response correlating to a first stage of the estrus phase of the estrous cycle prior to the LH peak is distinguishable to an unaided human eye from the color response correlating to a second stage of the estrus phase of the estrous cycle subsequent to the LH peak.

According to a sixth aspect of the invention, a method of inducing pregnancy in a mammal which exhibits an estrous cycle. The method involves monitoring the phase of an estrous cycle that the mammal is in at a given time that a biological sample is obtained from the mammal. The biological sample obtained from the mammal is combined with a flavonol and iodine to induce a reaction that provides a color response on a hydrophobic substrate. The estrus phase of the estrous cycle has a corresponding color response to the flavonol and the iodine that is distinguishable to an unaided human eye from the color responses of each other phase of the estrous cycle. The mammal is inseminated or bred at a point in time when the mammal is indicated to be in the estrus phase as reflected by the color response. In an exemplary embodiment of this sixth aspect, the flavonol is quercetin.

Other aspects of the invention, including apparatus, devices, indicators, kits, processes, and the like which constitute part of the invention, will become more apparent upon reading the following detailed description of the exemplary embodiments.

BRIEF DESCRIPTION OF THE DRAWING(S)

The patent or application file contains at least one drawing executed in color. Copies of this patent or patent application publication with color drawing(s) will be provided by the Office upon request and payment of the necessary fee.

Figure 3:
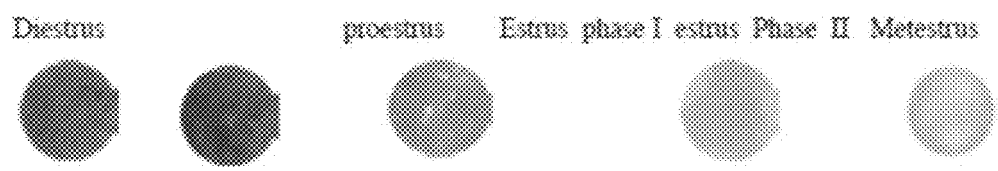
Figure 4:
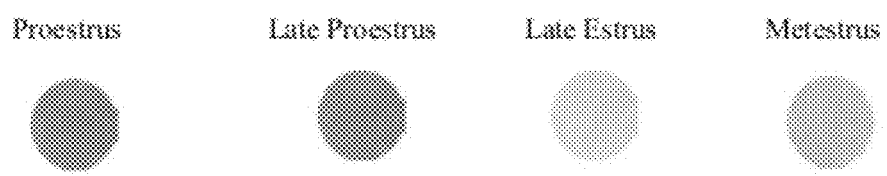
Figure 5:
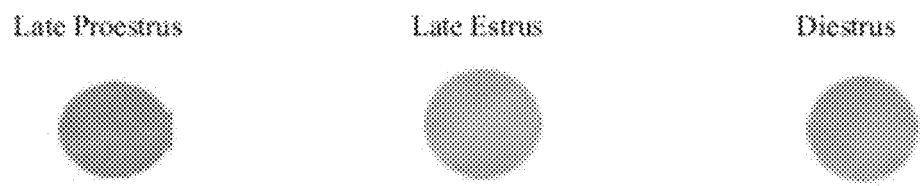

The accompanying drawings are incorporated in and constitute a part of the specification. The drawings, together with the general description given above and the detailed description of the exemplary embodiments and methods given below, serve to explain the principles of the invention. In such drawings:

FIG. 1 is a chart containing colored photographs showing the relationship between cycle phase and saliva color response for an example in which the saliva was treated with an anthocyanin pigment and a flavonol pigment;

FIG. 2 contains colored photographs showing the relationship between cycle phase and saliva color response for an example in which the saliva was treated with an anthocyanin pigment and divalent metal salt solution;

FIG. 3 contains colored photographs showing the relationship between cycle phase and cow saliva color response for an example in which the cow saliva was treated with a flavonol pigment and iodine;

FIG. 4 contains colored photographs showing the relationship between cycle phase and horse saliva color response for an example in which the horse saliva was treated with a flavonol pigment and iodine; and FIG. 5 contains colored photographs showing the relationship between cycle phrase and horse saliva color response for an example in which the horse saliva was treated with an anthocyanin pigment and a flavonol pigment.

DETAILED DESCRIPTION OF THE EXEMPLARY EMBODIMENTS AND EXEMPLARY METHODS

Reference will now be made in detail to exemplary embodiments and methods of the invention. It should be noted, however, that the invention in its broader aspects is not necessarily limited to the specific details, representative materials and methods, and illustrative examples shown and described in connection with the exemplary embodiments and methods.

Estrus detection as described herein may be used with various types of mammalian animals having estrous cycles, including for example cows, horses, swine, sheep, goats, laboratory animals such as rats, mice, and hamsters. It should be noted that exemplary embodiments of the invention are not applicable to saliva collected from guinea pigs because their saliva lacks the characteristic proline rich proteins that are sensitive to this assay. Because successful impregnation or breeding is most probable if it occurs during the second stage of the estrus phase, i.e., subsequent to the LH peak, it is desirable that the detection allow the tester to distinguish the first stage of the estrus phase (prior to the LH peak) from the second stage of the estrus phase in order to optimize insemination and breeding success rates.

The disciplines of estrous cycle monitoring and estrus phase detection are also useful in fields other than pregnancy inducement and mapping of different phases of the estrous cycle. For example, in carrying out laboratory experiments on animals such as mice, dogs, rats, etc., the particular estrous cycle phase of a laboratory animal is often an unknown variable that can influence the results of tests performed on the animal. By predetermining which phase of an estrous cycle a laboratory animal is in at the time of testing, the technician can schedule the substantive tests on the lab animals while each is in the same predetermined/preselected estrous cycle phase to thereby isolate this cycle-phase variable and thus prevent it from contributing to the variability of the test results.

The distinctive color responses corresponding to each phase of the estrous cycle also allows a farmer/breeder/caretaker to monitor for whether an animal is not cycling or has anestrous cycles. The breeder, for example, may take samples periodically (e.g., daily) and observe for color patterns relating to hormonal activity. Mammals that are not cycling generally will not display the above-described color patterns. An anestrous female will not demonstrate color change (i.e., the same continuous color response) over a time frame equivalent to an estrous cycle of that female species. Non-cycling and anestrous cycles may reflect nutritional deficiencies in the diet of the animal that require attention.

The selected biological sample preferably yet optionally is a non-invasive specimen that is attainable from the subject without requiring penetration of the skin, such as with a needle or scalpel as part of a surgical procedure. Preferably saliva is the non-invasive biological sample. While saliva is the biological sample used in most of the exemplary embodiments described herein, other biological samples, such as fluids (e.g., blood, vaginal fluid) and non-fluids (e.g., skin, etc.) may be selected. Saliva may be collected using known procedures, for example, by introducing an absorbent material such as a sponge into the mouth of the animal for a sufficient time to allow the sponge to absorb the saliva. The saliva collected from the subject is then extracted from the sponge, for example, by inserting the sponge into a device (e.g., syringe having a plunger) that can press the saliva into a collection vessel, such as an Eppendorfer tube. Alternatively, a portion or the entire estrus indicator may be directly inserted into and contacted with the inside of the animal's mouth to collect the saliva sample.

First Embodiment

In a first exemplary method a female mammal is monitored for the estrus phase of the female mammal's estrous cycle. The exemplary method features depositing a biological sample from the female mammal on a hydrophobic substrate during a phase of the estrous cycle, and contacting the biological sample with an anthocyanin pigment and a flavonol pigment to produce a color response indicative of the phase of the estrous cycle of the female mammal at the time the biological sample was collected. The color responses (see, e.g., FIG. 1) produced by the different phases of the estrous cycle are visually distinctive from one another to the unaided human eye. However, it should be understood that even though differences in color responses are observable to the unaided human eye, analyzing equipment such as colorimeters and spectrophotometers, while not generally necessary for carrying out this embodiment, optionally may be employed to distinguish between estrous cycle phases.

An exemplary substrate on which the biological sample is deposited for this first exemplary embodiment has a hydrophobic surface. Suitable substrate materials include polyethylene, glass, starch, and plastics such as styrene, polypropylene, or cyclo-olefins. Where the substrate is not hydrophobic, it may be modified or treated with a wetting agent (e.g., a surfactant or detergent) or covered with a hydrophobic surface layer. See, e.g., U.S. Pat. No. 4,125,673. For example, suitable substrates may be prepared by coating a base with a layer of 2% Methocel A (Dow chemical). Exemplary substrates are polyethylene plug, Porex X-4901, Porex X-4903, Porex X 4905, Porex 6410 (Porex Technologies) and similar pads having a porosity of about 50 microns or greater.

The hydrophobic substrate is inoculated with a flavonol. An exemplary flavonol suitable for this and other exemplary embodiments of the invention is quercetin.

For example, according to one exemplary procedure, $1 \times 10^{-5}$ molar concentration of quercetin is dissolved in ethanol mixed in a ratio by volume of 80:20, for ethanol mixed with a buffer at pH>8. 100 microliters of this solution is added to the hydrophobic substrate and allowed to dry at ambient conditions. The test sample is inoculated onto the hydrophobic surface that has been treated with the flavonol. The resulting color is yellow. In order read a color response that is unique to a particular phase of the estrous cycle, the assay is exposed to an anthocyanin pigment.

Generally, anthocyanin pigments useful for this first embodiment may possess the following structure:

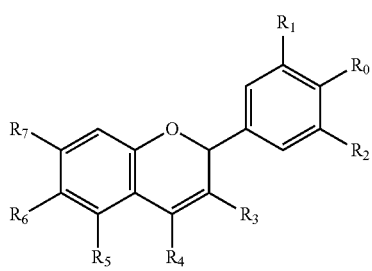

(Formula I)

wherein $R_0$ may be selected from the group consisting of hydrogen and hydroxy, but preferably is hydroxy; $R_1$ may be selected from the group consisting of hydrogen, hydroxy, and $C_1$-$C_4$ alkoxy such as methoxy; $R_2$ may be selected from the group consisting of hydrogen, hydroxy, and $C_1$-$C_4$ alkoxy such as methoxy; $R_3$ (appended to the three-position carbon) and $R_5$ (appended to the five-position carbon) each is an O-glycosyl group, wherein $R_3$ and $R_5$ may be the same or different relative to one another; $R_4$ is preferably hydrogen; $R_6$ may be selected from the group consisting of hydroxy and hydrogen; and $R_7$ is selected from the group consisting of hydrogen, hydroxy, and $C_1$-$C_4$ alkoxy, but preferably is a hydroxy group.

Using these pigments, the visible color response produced by the estrus phase of the estrous cycle is distinctive from the other phases. Hence, the visible color response permits the determination of the corresponding phase of the estrous cycle of the female mammal. Representative exemplary anthocyanins pigments of this first exemplary embodiment include cyanidin 3,5-diglucoside, petunidin-3,5-diglucoside, hirsutidin 3,5-diglucoside, pelargonidin 3,5-diglucoside, malvidin 3,5-diglucoside, and petunidin 3,5-diglucoside. These and other anthocyanins and other flavonoids described herein may be obtained from various commercial sources, such as, for example, Sigma Aldrich and Polyphenols in Norway. Alternative sources are also available. The anthocyanin is dissolved in methanol at $1 \times 10^{-3}$ molar concentration. Other alcohol solutions having molar concentrations of, for example, $10^{-1}$ M to $5 \times 10^4$ M are exemplary. Alternatively, the solution may be dried before it is deposited on the substrate.

As described above, pigments other than malvidin 3,5-diglucoside may be used in accordance with exemplary embodiments described herein. The particular color response pattern over the course of the estrous cycle may vary from one pigment to another. That is, the specific synchrony between proestrus, estrus, metestrus, and diestrus and their corresponding color responses for malvidin 3,5-diglucoside is not necessarily shared by other useful pigments. The matching of corresponding color response patterns to other anthocyanin-biological sample combinations may be determined, for example, by tracking color responses of the combinations relative to ovulation of the animal.

The color response reveals the phase of the estrous cycle of the mammal as of the time the sample was obtained, and allows the breeder or inseminator to determine when the estrus phase will occur. If the color response dictates that the animal is currently in the estrus phase, insemination may proceed or may be slightly delayed to correspond to the optimum time for insemination, i.e., after the LH peak. On the other hand, if the color response dictates that the animal is in proestrus, metestrus, or diestrus, a timetable for the animal's estrous cycle may be used to predict when estrus and ovulation may be expected. Optionally, testing can be repeated on a periodic (e.g., daily) basis up to the second stage of the estrus phase and/or ovulation to ensure that insemination or breeding is timely synchronized with the cycle.

Second Embodiment

According to a second exemplary embodiment, the biological sample obtained from the mammal is combined with an anthocyanin pigment and divalent metal salt solution (e.g., aqueous calcium chloride or zinc chloride) to induce a reaction that provides a color response on a hydrophobic substrate. The hydrophobic surface may be any of those described above in connection with the first embodiment. An exemplary anthocyanin pigment for this second embodiment is one having the structure of Formula I above, but in which the three-position carbon has an O-glycosyl group and the five-position carbon preferably does not have an O-glycosyl group. The five-position carbon substituent may be, for example, hydrogen, hydroxy, or alkoxy, such as methoxy.

The hydrophobic surface is treated with the metallic salt solution, preferably prior to exposure to the biological sample, particularly when the pigment selected has a three-position carbon with an O-glycosyl group and a five-position carbon with no O-glycosyl group. Saliva typically has a salt concentration between $1 \times 10^{-3}$ M and $1 \times 10^{-4}$ M. Salt concentration present in body fluid such as saliva will vary depending upon the time of day and flow rate when the saliva sample is collected. To eliminate natural fluctuations in the natural salt concentration as a variable in the testing procedure, the salt concentration of the saliva is optionally artificially raised above $1\times10^2$ M, such as into a range of about $1\times10^1$ M to about $5\times10^2$ M. Divalent metal salt solutions are particularly useful for this purpose.

It has been found that divalent salts such as calcium chloride, zinc chloride, zinc gluconate, and magnesium salts such as magnesium chloride yield conditions that allow the estrus phase to produce color responses that are visually distinct from the other phases of the estrous cycle. It has even been found that the color responses may uniquely correspond to each phase of the estrous cycle when the biological sample is exposed to the anthocyanin pigment with an 3-O-glycoside, no 5-O-glycoside, and a position 7-hydroxyl group, thus allowing for a distinct color response to represent each phase of the estrous cycle, and both stages of the estrus phase: one color for diestrus, one color for proestrus, one color for the first stage of the estrus phase prior to the LH peak, one color for the second stage of the estrus phase subsequent to the LH peak, and one color for metestrus, with each of the colors being visually distinguishable from one another, preferably to the unaided human eye. Calcium chloride ($1\times10^{-2}$ molar) has been found to be a particularly exemplary divalent metal salt solution, especially when the selected anthocyanin pigment is malvidin 3-glucoside.

In exemplary embodiments of the invention in which an anthocyanin is used, the anthocyanin pigment may be dissolved in an alcohol, such as methanol. Other forms of alcohol such as ethanol and isopropanol and other solvents may also be used. The anthocyanin pigment may be deposited as part of a solution, e.g., with the pigment dissolved in alcohol, or dispersed in a non-solvent. Alcohol solutions having molar concentrations of, for example, $10^{-1}$ M to $5\times10^4$ M are exemplary. Alternatively, the solution may be dried before it is deposited on the substrate.

For example, a hydrophobic substrate such as Porex X-6410 may be contacted with 20 microliters of 2% methyl cellulose mixed with a defined concentration of a divalent salt and allowed to dry at room temperature. This treated substrate is then stamped to form small discs that are placed in respective wells formed in the top of the titer plate. The titer plate containing the treated substrate discs in its wells can be stored in ambient conditions until the plate is ready for use. Optionally, the well may be pre-inoculated with the anthocyanin pigment in methanol, for example, with a concentration of $1\times10^{-3}$ M, and allowed to dry in ambient conditions. The biological sample such as saliva from a female mammal is deposited in the wells of the hydrophobic substrate and optionally dried and analyzed (or stored for later analysis). Exposure of the deposited biological sample to the pigment generates a color response that may be recorded. It should be understood that alternative sequences of processing steps may be practiced. For example, the divalent metal salt may be applied to the substrate before or after the biological sample is applied. Likewise the pigment may be deposited into the well before the biological sample is applied, or the pigment may be inoculated onto the hydrophobic substrate after the biological sample has been applied.

In this and other exemplary embodiments, the color response generally becomes discernible within 15 minutes after exposing the saliva or other biological sample to the pigment or combination of pigments. Depending upon the pigment, the color responses of the different cycle phases may be sufficiently distinctive that a person may observe and visually distinguish between the different color responses with the unaided human eye. However, it should be understood that analyzing equipment such as colorimeters and spectrophotometers, while not generally necessary, optionally may be employed.

Carrying out an example of the second exemplary embodiment in which malvidin-3-glucoside is selected as the anthocyanin and in which the substrate is pre-treated with dilute concentrations of calcium chloride or zinc chloride solution, distinct color responses are observed for each phase of the estrous cycle and in both stages of the estrus phase. These distinct color responses observed in cow saliva include: a blue-purple color response is produced during diestrus, a pale white color response is indicative of proestrus, a dark or aqua blue response is produced in the first stage of the estrus phase, a pale blue response is produced in the second stage of the estrus phase, and a pink response is indicative of a saliva sample obtained at the end of metestrus. As demonstrated by this example, distinguishable color responses does not necessarily mean different colors, but may mean different yet distinguishable shades of a color, such as in the case of the dark blue response of the first stage of the estrus phase and the pale blue response of the second stage of the estrus phase.

Without wishing to be bound by any theory, it is believed that these distinct color responses arise due to variations in mucin composition and structure. It is known that gylcosylation of mucins is altered during the estrous cycle. Braga Vania M. M. and Sandra J. Gendler, Modulation of Muc-1 Mucin Expression in the Mouse Uterus During Estrus, Early Pregnancy, and Placentation, Journal of Cell Sciences. Vol. 105, pp. 397-405 (1993). It is also known that estradiol affects membrane transport of salt in the biological sample which changes according to each phase of the estrous cycle. T. R. Ediger, W. L. Kraus, E. J. Weinman, and B. S. Katzenellenbogen, Estrogen Receptor Regulation of the Na+/H+ Exchanger Regulatory Factor, Endocrinology, Vol. 140, No. 7, pp. 2976-82 (1999). Changes in sodium and chlorine ions also affect the hydrophobic and hydrophilic properties of the mucins. Marie Skepo, Per Linse, and Thomas Arnebrant, Coarse-Grained Modeling of Proline Rich Protein1 (PRP-1) in Bulk Solution and Adsorbed to a Negatively Charge Surface, J. Phys. Chem. B., 110 (24) pp. 12141-12148 (2006). The structural changes in the mucins brought about by both degylcosylation and changes in salt concentration affect whether or not certain anthocyanins will either form intensely colored stacked complexes or remain uncomplexed ionic forms that give color responses reflective of their aqueous equilibrium state. P. Mazzaracchio, P. Pifferi, M. Kindt, A. Munyaneza, and G. Barbiroli, Interactions between Anthocyanins and Organic Food Molecules in Model Systems, International Journal of Food Science and Technology, Vol. 39, Issue 1, pp. 53-59 (2004).

The purple response of diestrus is generated by equilibrium between different forms of the anhydrobase forms of the anthocyanin. In proestrus, increased levels of estradiol results in enzyme production that removes certain sugar groups on the mucins, thus rendering these mucins hydrophobic and vulnerable to "aggregation" which results in the changes as to how anthocyanins respond to water, thereby causing degradation of any colored anthocyanin complexes. Saliva during the estrus phase shows no "aggregation" of mucins thus allowing for anthocyanins to form complexes that interact through "stacking" in association with a divalent metallic ion. This pigment "stacking" in the presence of a divalent ion allows for a stable dark blue response during the first stage of the estrus phase. As discussed in further detail below, as estrus progresses, the stacking interaction of the anthocyanin is reduced, which is reflected in appearance as a fading of the blue color response. Contacting the biological sample to a defined concentration of divalent metallic salt in the presence of the anthocyanin pigment further assists the breeder to distinguish the estrus phase from the diestrus and proestrus phase, and thereby facilitates more accurate prediction of when the estrus phase will occur.

For example, if the color response dictates that the animal is currently in the estrus phase, insemination or breeding may proceed or may be slightly delayed to correspond to the optimum time for insemination or breeding, i.e., after the LH peak. On the other hand, if the color response dictates that the animal is in proestrus, metestrus, or diestrus, a timetable for the animal's estrous cycle may be used to predict when the estrus phase and ovulation may be expected. Optionally, testing can be repeated on a periodic (e.g., daily) basis up to the second stage of the estrus phase and/or ovulation to ensure that insemination or breeding is timely synchronized with the cycle.

In the context of this second embodiment, anthocyanins having a three-position carbon with an O-glycosyl group and a five-position carbon with no O-glycosyl group are particularly effective in producing visible color responses for the first and second stages of the estrus phase, i.e., prior and subsequent to the LH peak, respectively, that are visually distinctive of one another to the unaided human eye. For example, using malvidin 3-glucoside, a deep blue color response is indicative of the first stage of the estrus phase (prior to the LH peak). The second stage of the estrus phase becomes visually discernible when the deep blue begins to fade to a pale blue. The second stage of the estrus phase up to approximately the onset of ovulation (including the beginning of ovulation) is the ideal time to inseminate a cow with demonstrated effectiveness. Thus, when the color response transitions from deep or dark blue to pale blue, the animal should be inseminated or bred immediately or soon thereafter, for example, within approximate 12 hours from obtaining the biological sample providing the pale blue response, and preferably within approximately 18 hours from then. The white color indicative of proestrus informs the breeder that estrus is possible in, for example, 24-36 hours after the biological sample has been collected so that the breeder may follow up with another test within that time frame. Pale blue informs the breeder that ovulation is imminent and now is the best time to inseminate. Pink is the color observed in metestrus and indicates that ovulation is occurring. Release of blood in the vagina is a sign that confirms that ovulation has occurred.

As described above, pigments other than malvidin 3-glucoside may be used in accordance with exemplary embodiments described herein. The particular color response pattern over the course of the estrous cycle may vary from one pigment to another. That is, the specific synchrony between proestrus, estrus, metestrus, and diestrus and their corresponding color responses of white, blue, pink, and purple for malvidin 3-glucoside are not necessarily shared by other useful pigments. The matching of color response patterns to other anthocyanin-biological sample combinations may be determined, for example, tracking color responses of the combinations relative to ovulation of the animal.

Third Embodiment

According to other exemplary embodiments, a flavonol may be selected as the pigment. Flavonols have a chemical structure similar to the anthocyanin structure described above, except that $R_4$ is a keto group and $R_3$ is usually a hydroxyl group (i.e., 3-hydroxyflavone).

Hydrophobic substrates and other testing procedures and parameters discussed above with respect to the first and second embodiments may be implemented in this third embodiment. For example, the flavonol pigment may be dissolved in an alcohol such as ethanol. Generally, the use of mono- and divalent metals is less important in this third embodiment in which a flavonol is used with iodine. The biological sample may be processed as described above in connection with the first and second embodiments.

As explained above, in accordance with exemplary methods the anthocyanins, flavonols, and other flavonoids produce a color response in synchrony with the different phases of the estrous cycle. Selection of quercetin followed by exposure to iodine resulted in a blue color response for diestrus, a golden brown color response for proestrus, and a clear color response for estrus, and yellow for metestrus.

The particular color responses each occur at a specific corresponding phase in the estrous cycle and thereby allow for accurate prediction as to when would be the best time for insemination or breeding of the subject animal from which the biological sample was obtained. In the event that the color response corresponds to the fertile late estrus phase of the cycle, artificial insemination may be carried out immediately. Where the test results indicate that the animal is in another phase of the estrous cycle, the result may be used to estimate how many days or hours are needed to reach late estrus for optimal insemination results. The accurate prediction of the estrus phase and ovulation can be used for any of the purposes discussed herein, e.g., to optimize efficiency of natural or artificial insemination and ultimately save the breeder (e.g., farmer, caretaker, etc.) time and money. Further, the testing procedure can be conducted without the expertise of a professional laboratory technician or specialized lab facilities, allowing for faster result turn-around times and thereby reducing missed opportunities for successful insemination.

The following examples are provided for purposes of explanation and elaboration, and are not exhaustive of the scope of the exemplary embodiments described herein.

The following saliva collection procedures are suitable for carrying out the examples. It should be understood that other procedures may be practiced in carrying out any embodiment (including the first, second and third embodiments) or example described herein. The saliva samples are obtained on a daily basis using a sponge. The sponge may be wetted, such as by rinsing it in about 1 ml distilled water one or more times. The sponge is inserted into a cow's mouth and held (and optionally moved) inside the mouth for a sufficient amount of time to absorb a saliva specimen, e.g., about 20-40 seconds. After being removed from the subject's mouth, the sponge may be inserted into a syringe. The plunger of the syringe is pushed to extract the saliva from the sponge into a suitable tube or other collection vessel. The sponge may then be discarded. The vessel may be appropriately marked, e.g., identification indicia, date, and time of collection. Generally, a sponge may yield about 3 ml of saliva. Optionally within several hours of collecting the saliva in a sponge, the sponge may be stored in a refrigerator for several hours. It is preferred not to store the sponge below freezing temperature. After the saliva has been extracted from the sponge, however, the saliva may be frozen until ready for testing.

EXAMPLES

Example 1

Embodiment 1: Anthocyanin/Flavonol

The surface of a polyethylene substrate was treated with 20 microliters of 2 weight percent A4C Methocel (Dow Chemical). Then 50 microliters of $1\times10^{-5}$ molar quercetin dissolved in ethanol/pH 8 buffer (80 vol %:20 vol %) combination was added. The surface of the treated substrate was inoculated with 50 microliters of cow saliva as obtained from inside the mouth of a cow. The assay was treated with 20 microliters of $1\times10^{-3}$ molar concentration of the pigment malvidin 3,5-diglycoside and the color response was recorded. The results are shown in FIG. 1 and set forth below in Table 1.

TABLE 1

| Cycle Phase | Color Response |
| --- | --- |
| Diestrus | Purple |
| Proestrus | Green |
| Estrus | Stage 1: pale green |
|  | Stage 2: yellow/Clear |
| Metestrus | Blue |
|  | Pink (at end of Metestrus Phase) |

In Example 1, the pale green and yellow/clear color responses of the first and second stages of the estrus phase or visually distinguishable to an unaided human eye from the purple, green, and blue/pink color responses of diestrus, proestrus, and metestrus, respectively. Further, the pale green response of the first stage of the estrus phase is visually distinguishable from the yellow/clear response of the second stage of the estrus phase.

Example 2

Embodiment 2: Anthocyanin/Divalent Metal Salt Solution

The surface of a polyethylene substrate was treated with 20 microliters of 2 weight percent A4C Methocel (Dow Chemical). Then, 20 microliters of $1\times10^{-1}$ (0.1) molar calcium chloride was applied to the undersurface of the treated substrate, and the substrate was dried. The upper surface of the treated substrate was inoculated with several microliters of saliva absorbed from the side of the mouth of a cow. The assay was treated with 20 microliters of $1\times10^{-3}$ molar concentration of the pigment malvidin 3-glycoside and the color response was recorded. The results are set forth below.

TABLE 2

| Cycle phase | Time | Color Response | Progesterone (ng/mg) | Estrogen (ng/mg) | Luteinizing hormone (LH) level (ng/mg) |
| --- | --- | --- | --- | --- | --- |
| Proestrus | Day 3 | Purple | <4 | >0.004 | >2 |
|  | Day -2 | Pale Purple | <2 |  |  |
|  | Day -1 | No color/white | <2 | 0.01 | 4 |
| Estrus | Day 0 8-30 hours | Deep blue 1$^{st}$ stage Pale blue 2$^{nd}$ stage | <2 | <0.002 | >10 |
| Ovulation | 10-14 hrs | Pink | <2 | <0.002 | <2 |
| Metestrus | 3-4 days | Pink-purple | 4 | 6 | <2 |
| Diestrus | 12-15 days | Blue-purple | >4 | 0.002 | <2 |

For example, a purple color response for cow saliva tested with malvidin 3-glucoside indicates not to inseminate the mammal. Pale white or no visible color indicates that the estrus phase is possibly within 24-36 hours. Deep blue indicates that the cow is in the estrus phase and insemination should be performed when the dark blue fades to pale within the next approximately 12-18 hours to coincide with ovulation. Pale blue indicates that ovulation is imminent and insemination should be performed immediately. A pinkish purple color indicates metestrus meaning that ovulation has occurred. The deep blue color response corresponding to the estrus phase is visually distinguishable to the unaided human eye from the corresponding color responses of the other phrases of the estrous cycle. Likewise, the deep blue and pale blue color responses corresponding to the first and second stages of the estrus phase are visually distinguishable from one another.

Colored photographs of the responses obtain from Example 2 are shown in FIG. 2.

Example 3

Embodiment 3: Flavonol/Iodine

The surface of Porex X-4904 filter was inoculated with $1\times10^{-3}$ molar quercetin and allowed to dry in ambient conditions. 50 microliters of saliva from a cow were pipetted onto the surface of the treated Porex. Next, 20 microliters of 10% tincture of iodine was pipetted onto the exposed Porex surface, and the color responses were recorded as follows:

TABLE 3

| Cycle Phase | Color Response |
| --- | --- |
| Diestrus | Blue-brown |
| Late Diestrus | Dark blue-brown |
| Proestrus | Green |
| Estrus | Clear |
| Metestrus | Yellow |

The color responses reported in Table 3 are shown in FIG. 3.

Example 4

The procedures of Example 3 were repeated with horse saliva. The results are shown in FIG. 4.

Example 5

Hypothetical Corresponding to Embodiment 1

A titer plate is treated with a defined concentration of malvidin 3,5-diglucoside dissolved in methanol. A sheet of Porex filter is soaked in $1\times10^{-5}$ molar quercetin and allowed to dry. Circular pieces of the Porex filter are punched out of the sheet and placed in respective wells of the titer plate. 20 microliters of 2% methocel is added to the Porex Filter. 40-50 microliter saliva samples are obtained from cows in different phases of their estrous cycles in accordance with the procedures described above. The saliva samples are added to respective wells. 50 microliters $1\times10^{-3}$ molar of anthocyanin pigment with 3,5-diglycosides dissolved in methanol is added. Alternatively, the anthocyanin pigment can be put onto a surface and allowed to dry. When the test sample is wet, it is contacted to the surface that has the anthocyanin pigment. After 15 minutes of exposure to the saliva, a color response was observed for each well. The saliva sample from the cow in early proestrus will produce a green color response. The saliva sample from the cow in diestrus will produce a purple color response. The saliva sample from the cow in the estrus phase will produce a pale green or yellow color response, depending upon whether the sample was taken before or after the LH peak. The saliva sample corresponding to the metestrus phase will produce a blue or pink response.

Example 6

Corresponding to Embodiment 1

Malvidin 3,5-digluoside (Poly Phenols) was mixed with methanol to prepare a $1\times10^{-3}$ molar solution. Quercetin (Sigma Aldrich) was weighed and mixed with ethanol and diluted in sodium hydroxide to prepare a $1\times10^{-3}$ molar solution. Porex 4901 was cut into a strip and coated with methocel 4AC (2%, Dow Chemical). After drying, the strip was soaked in the $1\times10^{-3}$ molar quercetin.

A saliva sample was absorbed from the mouth of a mouse using a "Q-tip." The wetted Q-tip was pushed own on the surface of the Porex filter, and absorption of the saliva sample onto the filter was noted by observation of a deepening of the yellow color of the quercetin on the filter. 1 microliter of $1\times10^{-3}$ malvidin 3,5-diglucoside was exposed to the wet spot of the filter. The saliva sample from the estrus phase produced a green color response that was visually distinguishable from the mostly purple color responses corresponding to the other phases of the estrous cycle.

Example 7

Corresponding to Embodiment 1

Saliva was collected from horses by inserting clean wet sponges into a horse's mouth. The sponge was removed and placed into a plunger which pushed the saliva into a 2 ml Eppendorfer tube. 20 microliters of the sample were pipetted onto the surface of a Porex X6410 filter that had been treated with 20 microliters of $1\times10^{-3}$ molar quercetin (dissolved in ethanol and buffer at pH=8 at 90:10 ratio). After 15 seconds, 20 microliters of $1\times10^{-3}$ molar malvidin 3,5-diglucoside was pipetted onto the Porex filter treated with the saliva and quercetin. The recorded color responses were aqua green for late proestrus, blue-gray for second stage of the estrus phase, and faded purple for diestrus. The results are shown in FIG. 5.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. The specification describes specific examples to accomplish a more general goal that may be accomplished in another way.

Only those claims which use the words "means for" are to be interpreted under 35 USC 112, sixth paragraph. Moreover, no limitations from the specification are to be read into any claims, unless those limitations are expressly included in the claims.

What is claimed is:

1. A method of determining the phase of an estrous cycle that a mammal is in at a given time that a biological sample is obtained from the mammal, comprising combining the biological sample obtained from the mammal with an anthocyanin pigment and flavonol pigment to induce a reaction that provides a color response on a hydrophobic substrate, the estrus phase of the estrous cycle having a corresponding color response to the anthocyanin pigment and the flavonol that is distinguishable to an unaided human eye from the color responses of each other phase of the estrous cycle, and correlating the corresponding color response to the estrus phase of the estrous cycle.

2. The method of claim 1, wherein each phase of the estrous cycle has a corresponding color response that is distinguishable to the unaided human eye from the color responses of each other phase of the estrous cycle.

3. The method of claim 1, wherein the anthocyanin pigment has a three-position carbon with a first O-glycosyl group and a five-position carbon with a second O-glycosyl group.

4. The method of claim 3, wherein the anthocyanin pigment comprises a member selected from the group consisting of cyanidin 3,5-diglycoside, petunidin 3,5-diglycoside, hirsutidin 3,5-diglycoside, pelargonidin 3,5-diglycoside, and malvidin 3,5-diglycoside.

5. The method of claim 3, wherein the color response correlating to a first stage of the estrus phase of the estrous cycle prior to a luteinizing hormone peak and the color response correlating to a second stage of the estrus phase of the estrous cycle subsequent to the luteinizing hormone peak are visually distinctive from one another to the unaided human eye.

6. The method of claim 1, wherein the flavonol pigment comprises quercetin.

7. The method of claim 1, wherein the biological sample comprises saliva.

8. A method of inducing pregnancy in a mammal which exhibits an estrous cycle, comprising:
  determining according to the method of claim 1 the phase of an estrous cycle that the mammal is in at a given time that a biological sample is obtained from the mammal; and
  inseminating or breeding the mammal at a point in time when the mammal is indicated to be in the estrus phase as reflected by the corresponding color response.

9. The method of claim 1, wherein the biological sample comprises vaginal fluid.

10. A method of determining the phase of an estrous cycle that a mammal is in at a given time that a biological sample is obtained from the mammal, comprising combining the biological sample obtained from the mammal with a flavonol and iodine to induce a reaction that provides a color response on a hydrophobic substrate, the estrus phase of the estrous cycle having a corresponding color response to the flavonol and iodine that is distinguishable to an unaided human eye from the color responses of each other phase of the estrous cycle, and correlating the corresponding color response to the estrus phase of the estrous cycle.

11. The method of claim 10, wherein each phase of the estrous cycle has a corresponding color response that is distinguishable to the unaided human eye from the color responses of each other phase of the estrous cycle.

12. The method of claim 10, wherein the flavonol comprises quercetin.

13. A method of inducing pregnancy in a mammal which exhibits an estrous cycle, comprising:
  determining according to the method of claim 12 the phase of an estrous cycle that the mammal is in at a given time that a biological sample is obtained from the mammal; and
  inseminating or breeding the mammal at a point in time when the mammal is indicated to be in the estrus phase as reflected by the color response.

14. The method of claim 10, wherein the biological sample comprises vaginal fluid.

15. A method of determining the phase of an estrous cycle that a mammal is in at a given time that a biological sample is obtained from the mammal, comprising combining the biological sample obtained from the mammal with a flavonol pigment and a member selected from the group consisting of an anthocyanin pigment and iodine to induce a reaction that provides a color response on a hydrophobic substrate, the estrus phase of the estrous cycle having a corresponding color response that is distinguishable to an unaided human eye from the color responses of each other phase of the estrous cycle, and correlating the corresponding color response to the estrus phase of the estrous cycle.

16. The method of claim 15, wherein each phase of the estrous cycle has a corresponding color response that is distinguishable to the unaided human eye from the color responses of each other phase of the estrous cycle.

17. The method of claim 15, wherein the flavonol comprises quercetin.

18. A method of inducing pregnancy in a mammal which exhibits an estrous cycle, comprising:

determining according to the method of claim 15 the phase of an estrous cycle that the mammal is in at a given time that a biological sample is obtained from the mammal; and inseminating or breeding the mammal at a point in time when the mammal is indicated to be in the estrus phase as reflected by the color response.

\* \* \* \* \*